United States Patent
Zhang et al.

(10) Patent No.: US 10,337,033 B2
(45) Date of Patent: Jul. 2, 2019

(54) CARBONYL REDUCTASE OLIGOMERS AND THEIR APPLICATION IN SYNTHESIS OF CHIRAL ALCOHOLS

(71) Applicants: Rongzhen Zhang, Wuxi (CN); Yan Xu, Wuxi (CN); Kunpeng Li, Wuxi (CN)

(72) Inventors: Rongzhen Zhang, Wuxi (CN); Yan Xu, Wuxi (CN); Kunpeng Li, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 15/650,852

(22) Filed: Jul. 15, 2017

(65) Prior Publication Data

US 2018/0187217 A1   Jul. 5, 2018

(30) Foreign Application Priority Data

Dec. 30, 2016   (CN) .......................... 2016 1 1250627

(51) Int. Cl.
| | | |
|---|---|---|
| *C12N 9/04* | (2006.01) | |
| *C12P 7/04* | (2006.01) | |
| *C12N 9/02* | (2006.01) | |
| *C07C 29/143* | (2006.01) | |
| *C12N 9/52* | (2006.01) | |
| *C12P 7/22* | (2006.01) | |
| *C07C 33/26* | (2006.01) | |
| *C07K 2/00* | (2006.01) | |
| *C12N 15/70* | (2006.01) | |
| *C12Q 1/686* | (2018.01) | |

(52) U.S. Cl.
CPC .............. *C12P 7/04* (2013.01); *C07C 29/143* (2013.01); *C12N 9/0006* (2013.01); *C12N 9/0008* (2013.01); *C12N 9/52* (2013.01); *C12P 7/22* (2013.01); *C12Y 304/2207* (2013.01); *C07B 2200/07* (2013.01); *C07C 33/26* (2013.01); *C07K 2/00* (2013.01); *C12N 15/70* (2013.01); *C12Q 1/686* (2013.01)

(58) Field of Classification Search
None
See application file for complete search history.

(56) References Cited

U.S. PATENT DOCUMENTS 8,236,925 B1 * 8/2012 Wagner .............. A61K 49/0036
530/323

OTHER PUBLICATIONS

H. Mao et al. "Sortase-Mediated Protein Ligation: A New Method for Protein Engineering", J. Am. Chem. Soc. 126:2670-2671 and supporting Information pp. S1-S5. (Year: 2004).*
K. Chen et al. "Carbonyl reductase identification and development of whole-cell biotransformation for highly efficient synthesis of (R)-[3,5-bis(trifluoromethyl)phenyl] ethanol", Microbial Cell Factories 15:191. pp. 1-11. Nov. 11, 2016 (Year: 2016).*
K. Li et al., "Sortase A-mediated crosslinked short-chain dehydrogenases/ reductases as novel biocatalysts with improved thermostability and catalytic efficiency", Scientific Reports 7:3081 pp. 1-11 (Year: 2017).*
K. Li et al., "Sortase A-mediated oligomers of (S)-carbonyl reductase II suitable for biotransformation of (S)-phenyl-1, 2-ethanediol", Weishengwu Xuebao, 57(12): 1853-1864. Provided with Biosis abstract and Google translation (Year: 2017).*
Revision History for GenBank Accession: AB183149, retrieved from https://www.ncbi.nlm.nih.gov/nuccore/AB183149.1?report=girevhist on Mar. 19, 2019 (Year: 2019).*
Revision History for GenBank Accession: E59061, retrieved from https://www.ncbi.nlm.nih.gov/nuccore/E59061.1?report=girevhist on Mar. 19, 2019 (Year: 2019).*
Revision History for GenBank Accession: FJ939565, retrieved from https://www.ncbi.nlm.nih.gov/nuccore/FJ939565.1?report=girevhist on Mar. 19, 2019 (Year: 2019).*
Revision History for GenBank Accession: FJ939564, retrieved from https://www.ncbi.nlm.nih.gov/nuccore/FJ939564.1?report=girevhist on Mar. 19, 2019 (Year: 2019).*

* cited by examiner

*Primary Examiner* — Rebecca E Prouty
(74) *Attorney, Agent, or Firm* — Lili Chen

(57) ABSTRACT

Disclosed are methods for the synthesis of chiral alcohols by Sortase A-mediated oxidoreductase oligomers, which relates to the field of biocatalysis. In the present disclosure, oxidoreductase oligomers were used as biocatalysts for chiral alcohol preparation. Compared to wild-type enzymes, the oxidoreductase oligomers significantly improved catalytic activity and thermal stability. The sortase A-mediated oxidoreductase oligomers had 6-8 folds improvement in specific activity over that of the wild-type enzymes. The oligomers displayed a $T_m$ value 6-12° C. higher than that of the wild-type, suggesting the sortase A-mediated oxidoreductase oligomers significantly improved thermostability of the enzymes. The oxidoreductase oligomers catalyzed asymmetric transformation to produce (S)-1-phenyl-1,2-ethanediol or (R)-1-phenethyl alcohol within 3-6 hr, with an optical purity of 98%-100% and a yield of 98%-99%.

7 Claims, No Drawings

Specification includes a Sequence Listing.

SEQUENCE LISTING

<160> NUMBER OF SEQ ID NOS: 21

<210> SEQ ID NO 1
<211> LENGTH: 279
<212> TYPE: PRT
<213> ORGANISM: artificial sequence
<220> FEATURE:
<223> OTHER INFORMATION: Modified Protein Sequence

<400> SEQUENCE: 1

```
Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95
```

```
Ser Val Glu Glu Thr Ile Ser Gln Gln Glu Lys Asp Phe Gly Thr Ile
            100                 105                 110

Asp Val Phe Val Ala Asn Ala Gly Val Pro Trp Thr Glu Gly Pro Glu
            115                 120                 125

Ile Asn Val Asp Asn Tyr Asp Ser Trp Asn Lys Ile Ile Asn Leu Asp
130                 135                 140

Leu Asn Gly Val Tyr Tyr Cys Ala His Thr Val Gly Lys Ile Phe Lys
145                 150                 155                 160

Lys Asn Gly Lys Gly Ser Leu Val Ile Thr Ser Ser Met Ser Gly Thr
                165                 170                 175

Ile Val Asn Val Pro Gln Leu Gln Ala Ala Tyr Asn Ala Ala Lys Ala
            180                 185                 190

Ala Cys Thr His Leu Thr Lys Ser Leu Ala Val Glu Trp Ala Pro Phe
            195                 200                 205

Ala Arg Val Asn Cys Val Ser Pro Gly Tyr Ile Ala Thr Glu Ile Ser
            210                 215                 220

Asp Phe Val Glu Lys Asp Met Lys Ala Lys Trp Trp Gln Leu Thr Pro
225                 230                 235                 240

Leu Gly Arg Glu Gly Leu Ala Gln Glu Leu Val Gly Ala Tyr Leu Tyr
                245                 250                 255

Leu Ala Ser Asn Ala Ser Thr Tyr Thr Thr Gly Ala Asn Leu Ala Val
                260                 265                 270

Asp Gly Gly Tyr Thr Cys Pro
                275

<210> SEQ ID NO 2
<211> LENGTH: 5
<212> TYPE: PRT
<213> ORGANISM: artificial sequence
<220> FEATURE:
<223> OTHER INFORMATION: synthetic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Pro Xaa Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic sequence

<400> SEQUENCE: 3

Leu Pro Glu Thr Gly
1               5

<210> SEQ ID NO 4
<211> LENGTH: 148
<212> TYPE: PRT
<213> ORGANISM: Staphylococcus aureus

<400> SEQUENCE: 4

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
```

```
                    20                  25                  30
Pro Ala Thr Pro Glu Gln Leu Asn Arg Gly Val Ser Phe Ala Glu Glu
         35                  40                  45

Asn Glu Ser Leu Asp Asp Gln Asn Ile Ser Ile Ala Gly His Thr Phe
 50                  55                  60

Ile Asp Arg Pro Asn Tyr Gln Phe Thr Asn Leu Lys Ala Ala Lys Lys
 65                  70                  75                  80

Gly Ser Met Val Tyr Phe Lys Val Gly Asn Glu Thr Arg Lys Tyr Lys
                 85                  90                  95

Met Thr Ser Ile Arg Asp Val Lys Pro Thr Asp Val Gly Val Leu Asp
            100                 105                 110

Glu Gln Lys Gly Lys Asp Lys Gln Leu Thr Leu Ile Thr Cys Asp Asp
        115                 120                 125

Tyr Asn Glu Lys Thr Gly Val Trp Glu Lys Arg Lys Ile Phe Val Ala
    130                 135                 140

Thr Glu Val Lys
145

<210> SEQ ID NO 5
<211> LENGTH: 28
<212> TYPE: DNA
<213> ORGANISM: Artificial Sequence
<220> FEATURE:
<223> OTHER INFORMATION: DNA primer

<400> SEQUENCE: 5
cgccatatgc aagctaaacc tcaaattc                                    28

<210> SEQ ID NO 6
<211> LENGTH: 27
<212> TYPE: DNA
<213> ORGANISM: Artificial Sequence
<220> FEATURE:
<223> OTHER INFORMATION: DNA primer

<400> SEQUENCE: 6
ccgctcgagt ttgacttctg tagctac                                     27

<210> SEQ ID NO 7
<211> LENGTH: 35
<212> TYPE: DNA
<213> ORGANISM: Artificial Sequence
<220> FEATURE:
<223> OTHER INFORMATION: DNA Primer

<400> SEQUENCE: 7
cgggatccat gggaggcgga acatttacag tggtg                            35

<210> SEQ ID NO 8
<211> LENGTH: 53
<212> TYPE: DNA
<213> ORGANISM: Artificial Sequence
<220> FEATURE:
<223> OTHER INFORMATION: DNA primer

<400> SEQUENCE: 8
cggaattcgc cgccggtttc cggaaggctg ccaccgccac ccccacggta cgc         53

<210> SEQ ID NO 9
<211> LENGTH: 40
<212> TYPE: DNA
<213> ORGANISM: Artificial Sequence
```

<220> FEATURE:
<223> OTHER INFORMATION: DNA Primer

<400> SEQUENCE: 9
cgggatccat gggaggcgga acgtttcagc attttttaag         40

<210> SEQ ID NO 10
<211> LENGTH: 59
<212> TYPE: DNA
<213> ORGANISM: Artificial Sequence
<220> FEATURE:
<223> OTHER INFORMATION: DNA Primer

<400> SEQUENCE: 10
ccctcgaggc cgccggtttc cggaaggctg ccaccgccac caacgcaagt gtacccacc    59

<210> SEQ ID NO 11
<211> LENGTH: 40
<212> TYPE: DNA
<213> ORGANISM: Artificial Sequence
<220> FEATURE:
<223> OTHER INFORMATION: DNA primer

<400> SEQUENCE: 11
cgggatccat gggaggcgga agtaaagacg aaacaatttc         40

<210> SEQ ID NO 12
<211> LENGTH: 58
<212> TYPE: DNA
<213> ORGANISM: Artificial Sequence
<220> FEATURE:
<223> OTHER INFORMATION: DNA primer

<400> SEQUENCE: 12
ccctcgaggc cgccggtttc cggaaggctg ccaccgccac ctgggacagt ataaccac    58

<210> SEQ ID NO 13
<211> LENGTH: 20
<212> TYPE: DNA
<213> ORGANISM: Artificial Sequence
<220> FEATURE:
<223> OTHER INFORMATION: DNA primer

<400> SEQUENCE: 13
cccatgggcg aaatcgaatc         20

<210> SEQ ID NO 14
<211> LENGTH: 62
<212> TYPE: DNA
<213> ORGANISM: Artificial Sequence
<220> FEATURE:
<223> OTHER INFORMATION: DNA Primer

<400> SEQUENCE: 14
ccctcgaggc cgccggtttc cggaaggctg ccaccgccac ctggacaagt gtaaccacca    60
tc    62

<210> SEQ ID NO 15
<211> LENGTH: 62
<212> TYPE: DNA
<213> ORGANISM: Artificial Sequence
<220> FEATURE:
<223> OTHER INFORMATION: DNA primer

<400> SEQUENCE: 15

```
cccctcgaggc cgccggtttc cggaaggctg ccaccgccac ctggacaagt gtaaccacca    60
tc                                                                    62
```

<210> SEQ ID NO 16
<211> LENGTH: 58
<212> TYPE: DNA
<213> ORGANISM: Artificial Sequence
<220> FEATURE:
<223> OTHER INFORMATION: DNA primer

<400> SEQUENCE: 16

```
cccctcgaggc cgccggtttc cggaaggctg ccaccgccac ctggacaggt gaatccac      58
```

<210> SEQ ID NO 17
<211> LENGTH: 5
<212> TYPE: PRT
<213> ORGANISM: Artificial Sequence
<220> FEATURE:
<223> OTHER INFORMATION: Synthetic sequence

<400> SEQUENCE: 17

```
Gly Gly Gly Gly Ser
1               5
```

<210> SEQ ID NO 18
<211> LENGTH: 281
<212> TYPE: PRT
<213> ORGANISM: Candida parapsilosis

<400> SEQUENCE: 18

```
Met Ser Lys Asp Glu Thr Ile Ser Tyr Cys Asn Asp Gln Leu Gly Pro
1               5                   10                  15

Leu Pro Thr Thr Ala Pro Lys Val Ser Asp Asn Val Thr Asp Leu Phe
            20                  25                  30

Ser Phe Lys Gly Lys Val Val Ser Val Thr Gly Ser Ser Gly Gly Ile
        35                  40                  45

Gly Trp Ala Val Ala Glu Gly Phe Ala Gln Ala Gly Ala Asp Val Ala
    50                  55                  60

Ile Trp Tyr His Ser His Asn Ala Asp Glu Lys Ala Lys Tyr Leu Gln
65                  70                  75                  80

Glu Lys Tyr Gly Val Lys Ser Ile Ala Tyr Gly Cys Asn Ile Gly Val
                85                  90                  95

Ala Glu Glu Val Gln Lys Thr Val Asp Gln Ile Glu Ser Asp Phe Gly
            100                 105                 110

Lys Ile Asp Val Phe Val Ala Asn Ala Gly Ile Pro Trp Thr Asp Gly
        115                 120                 125

Pro Glu Ile Asp Val Gln Asp Leu Ser Lys Trp Thr Lys Ile Ile Asp
    130                 135                 140

Thr Asp Leu Asn Ser Val Tyr Tyr Cys Ala His Ala Ile Gly Pro Ile
145                 150                 155                 160

Phe Arg Lys Gln Gly Lys Gly Ser Leu Val Ile Thr Ala Ser Met Ser
                165                 170                 175

Ala Thr Ile Val Asn Val Pro Gln Leu Gln Ala Ala Tyr Asn Val Ala
            180                 185                 190

Lys Ala Gly Val Lys His Leu Ser Lys Ser Leu Ala Val Glu Trp Ala
        195                 200                 205

Pro Phe Ala Arg Val Asn Ser Val Ser Pro Gly Tyr Ile Ser Thr Asn
    210                 215                 220
```

```
Leu Thr Thr Phe Ala Asn Pro Asp Leu Gln Lys Lys Trp Val Gln Leu
225                 230                 235                 240

Thr Pro Leu Gly Arg Glu Gly His Pro Lys Glu Leu Val Gly Ala Tyr
            245                 250                 255

Leu Tyr Leu Ala Ser Asp Ala Ala Thr Phe Thr Thr Gly Cys Asp Leu
        260                 265                 270

Ala Val Asp Gly Gly Tyr Thr Val Pro
        275                 280
```

<210> SEQ ID NO 19
<211> LENGTH: 279
<212> TYPE: PRT
<213> ORGANISM: Candida parapsilosis

<400> SEQUENCE: 19

```
Met Gly Glu Ile Glu Ser Tyr Cys Asn Lys Glu Leu Gly Pro Leu Pro
1               5                   10                  15

Thr Lys Ala Pro Thr Leu Ala Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Ile Pro Trp Ala Asp Gly Pro Val
        115                 120                 125

Ile Asp Leu Glu Asn Tyr Asp Ala Trp Asn Lys Leu Ile Asn Thr Asp
130                 135                 140

Ile Asn Gly Val Phe Tyr Cys Ala His Ser Ile Gly Lys Ile Phe Lys
145                 150                 155                 160

Lys Asn Gly Lys Gly Ser Leu Ile Ile Thr Ala Ser Leu Ala Gly Ser
                165                 170                 175

Val Val Thr Ile Pro Gln Gln Gln Thr Pro Tyr Asn Thr Ala Lys Ala
            180                 185                 190

Ala Cys Leu His Leu Ala Lys Ser Leu Ala Val Glu Trp Ala Pro Phe
        195                 200                 205

Ala Arg Val Asn Thr Val Ser Pro Gly Tyr Phe Glu Thr Glu Ile Asn
210                 215                 220

Gly Phe Ala Asp Glu Asp Met Arg Glu Lys Trp Tyr Gln Leu Thr Pro
225                 230                 235                 240

Leu Gly Arg Met Gly Ile Thr Glu Glu Leu Val Gly Gly Tyr Leu Tyr
                245                 250                 255

Phe Ala Ser Asn Ala Ser Thr Phe Thr Thr Gly Ser Asp Leu Ile Ile
            260                 265                 270

Asp Gly Gly Phe Thr Cys Pro
        275
```

<210> SEQ ID NO 20
<211> LENGTH: 345
<212> TYPE: PRT
<213> ORGANISM: Kluyveromyces marxianus

<400> SEQUENCE: 20

| Met | Thr | Phe | Thr | Val | Val | Thr | Gly | Ala | Asn | Gly | Tyr | Ile | Ala | Lys | His |
|---|---|---|---|---|---|---|---|---|---|---|---|---|---|---|---|
| 1 | | | | 5 | | | | | 10 | | | | | 15 | |

Ile Leu Lys Ser Leu Leu Glu Asp Gly His Arg Val Ile Gly Thr Val
            20                  25                  30

Arg Asn Ser Lys Lys Ala Glu Glu Leu Lys Arg Thr Val Asn Asp Glu
            35                  40                  45

Asn Leu Ile Val Glu Leu Val Pro Asp Met Leu Val Glu Asn Ala Phe
 50                      55                  60

Asp Glu Leu Phe Lys Lys Tyr Asn Thr Gln Ile Lys Tyr Val Phe His
 65                      70                  75                  80

Thr Ala Ser Pro Val Leu Glu Thr Ser Lys Asp Tyr Glu Lys Ser Leu
                    85                  90                  95

Ile Glu Pro Ala Ile Thr Gly Ala Lys Ser Met Val Glu Ala Ile Arg
                100                 105                 110

Lys Tyr Ser Leu Thr Ser Val Glu His Ile Val Tyr Thr Ser Ser Ile
            115                 120                 125

Ala Ala Ser Ser Leu Glu Ser Glu Phe Thr Asp Pro Thr Leu Val Val
130                 135                 140

Ser Glu Asp Ser Trp Asn Pro Gln Gly Leu Glu Glu Ala Lys Thr Glu
145                 150                 155                 160

Phe Phe Thr Ala Tyr Ser Tyr Ser Lys Lys Ile Ala Glu Lys Thr Met
                    165                 170                 175

Trp Asp Phe Val Glu Glu Tyr Lys Gly Thr Glu His Glu Ile Lys Leu
                180                 185                 190

Thr Thr Val Asn Pro Cys Phe Asn Ile Gly Pro Gln Ala Tyr Glu Ala
            195                 200                 205

Asp Val Thr Glu Thr Met Asn Phe Thr Ala Glu Leu Ile Asn His Val
210                 215                 220

Val Lys Ser Lys Val Gly Asp Pro Leu Pro Pro Thr Arg Ile Val Pro
225                 230                 235                 240

Tyr Val Asp Val Arg Asp Thr Ala Arg Ala His Val Asp Ala Leu Lys
                    245                 250                 255

Asn Glu Lys Leu Ala Phe Gln Arg Leu Leu Val Val Gly Pro Phe Leu
                260                 265                 270

Ser Ser Gln Gln Ile Tyr Asp Ile Val Asn Glu Arg Phe Pro Gln Leu
            275                 280                 285

Arg Gly Lys Ile Ala Arg Gly Glu Pro Gly Ser Asp Lys Leu Asp Pro
290                 295                 300

Ala Lys Leu Ala Lys Phe Asp His Ala Arg Thr Thr Gln Ala Leu Gly
305                 310                 315                 320

Trp Glu Phe Thr Pro Ile Glu Lys Ala Ile Ala Asp Glu Val Ala Gln
                    325                 330                 335

Ile Leu Arg Val Gly Ala Tyr Arg Gly
            340                 345

<210> SEQ ID NO 21
<211> LENGTH: 292
<212> TYPE: PRT
<213> ORGANISM: Kluyveromyces aestuarii

<400> SEQUENCE: 21

Met Thr Phe Gln His Phe Leu Arg Gly Gly Leu Glu Asp Lys Thr Val
1               5                   10                  15

-continued

```
Pro Gln Glu Pro Pro Lys Glu Gln Tyr Pro Asp Gly Val Asn Tyr Leu
            20              25              30

Ser Leu Phe Ser Gln Lys Gly Lys Leu Thr Val Ile Thr Gly Gly Ala
            35              40              45

Gly Ala Ile Gly Gly Ala Leu Cys Glu Gly Phe Ala Ser Cys Gly Ser
    50              55              60

Asp Val Val Ile Leu Asp Tyr Lys Tyr Ser Pro Glu Leu Ser Ser Val
65              70              75              80

Leu Glu Ser Arg Tyr Gly Val Arg Ser Lys Ser Tyr Gln Val Asp Ile
            85              90              95

Thr Ser Ser Glu Asp Val Lys Leu Val Val Ala Lys Ile Leu Glu Asp
            100             105             110

Phe Pro Asp Arg Asp Ile Asn Thr Phe Val Ala Asn Ala Gly Ile Ala
            115             120             125

Trp Thr Asn Gly Ser Ile Leu Asn Glu Asn Ala Thr Pro Asp Val Trp
    130             135             140

Lys Arg Val Met Asp Val Asn Val Gln Gly Thr Tyr His Cys Ala Lys
145             150             155             160

Tyr Val Ala Glu Val Phe Lys Gln Gln Gly His Gly Asn Leu Ile Leu
            165             170             175

Thr Ala Ser Met Ser Ser Tyr Ile Ser Asn Val Pro Asn Tyr Gln Thr
            180             185             190

Cys Tyr Asn Ala Ser Lys Ala Ala Val Arg His Met Ala Lys Gly Phe
        195             200             205

Ala Val Glu Phe Ala His Leu Thr Asn Pro Ala Gly Lys Ile Arg Cys
    210             215             220

Asn Ser Val Ser Pro Gly Tyr Thr Asp Thr Ala Leu Ser Ala Phe Val
225             230             235             240

Pro Val Glu Gln Arg Ala Gln Trp Trp Gly Leu Thr Pro Met Gly Arg
            245             250             255

Glu Ala Leu Pro Gln Glu Leu Val Gly Ala Tyr Leu Tyr Leu Ala Ser
            260             265             270

Asp Ala Ala Ser Phe Thr Asn Gly Cys Asp Ile Gln Val Asp Gly Gly
        275             280             285

Tyr Thr Cys Val
    290
```

US 10,337,033 B2

CARBONYL REDUCTASE OLIGOMERS AND THEIR APPLICATION IN SYNTHESIS OF CHIRAL ALCOHOLS

CROSS-REFERENCES AND RELATED APPLICATIONS

This application claims the benefit of priority to Chinese Application No. 201611250627.8, entitled "Carbonyl reductase oligomers and their application in synthesis of chiral alcohols", filed Dec. 30, 2016, which is herein incorporated by reference in its entirety.

BACKGROUND OF THE INVENTION

Field of the Invention

The present invention relates to the field of asymmetric biosynthesis, which relates to a method for synthesis of chiral alcohols by sortase A-mediated oxidoreductase oligomers.

Description of the Related Art

Chiral compounds have been applied to the production of exquisite chemicals such as drugs, pesticides, hormone and food additives. For example, optically pure phenylglycol is not only a necessary chiral additive, but also the important intermediate of drugs, pesticides and functional materials with optical activity.

Some of Oxidoreductases have high stereoselectivity and can be applied to biotransformation of chiral compounds. For example, (S)-carbonyl reductase II (SCRII) from *Candida parapsilosis* CCTCC M203011 catalyzes reduction of 2-hydroxyacetophenone (2-HAP) to (S)-1-phenyl-1,2-ethanediol ((S)-PED). However, the (S)-PED production requires a long period of time (e.g. 48 hr) and with low efficiency. The recombinant *Saccharomyces cerevisiae*-SCRII and *Pichia pastoris*-SCRII also catalyzed the biotransformation of (S)-PED with relatively low efficiency. Recently, inventors expressed SCRII in *C. parapsilosis* CCTCC M203011 to improve enzyme activity by about 2 fold. But the biotransformation reaction required 24 hr. Therefore, it is necessary to modify SCRII to obtain more efficient oxidoreductases using protein engineering techniques.

In recent years, protein ligation has been increasingly used in biochemistry field. Peptide analogues and molecular probe can be specifically added to terminus of protein to acquire new functions. Sortase A (SrtA) from *Staphylococcus aureus* is used for protein ligation, which is a special and efficient method. SrtA can recognize the signal sequence LPXTG (X can be any amino acids) and cleave the amido bond between Thr and Gly to get a thioester intermediate. Then oligo-Gly can act as nucleophile to attack thioester intermediate to make protein ligate through the Gly. If the oligo-Gly is added to molecular probes like fluorescein and biotin, specific labeling in protein can be achieved.

DETAILED DESCRIPTION

To resolve the above mentioned problems, SrtA coding gene was cloned from *S. aureus* genome and expressed in *Escherichia coli*. Meanwhile, the signal peptide LPETG was added to C-terminus of SCRII using genetic technique. On one hand, SrtA can recognize the signal sequence LPETG at the C-terminus of SCRII and cleave the amido bond between Thr and Gly to get a thioester intermediate; on the other hand, a native Gly at N-terminus of the other SCRII act as nucleophile to attack thioester intermediate to make the two SCRII ligation to generate SCRII oligomer. The generated SCRII oligomer has improved thermostability and chiral synthesis efficiency. The SCRII oligomer catalyzed 2-HAP to (S)-PED with a yield and an optical purity of over 99% within 3 hr. Compared with recombinant *E. coli*-SCRII, the biotransformation reaction time was decreased by 16-fold.

SrtA-mediated ligation was applied to several other oxidoreductases, such as CR2 of SEQ ID NO: 20 (encoded by Genbank gene ID AB183149), CR4 of SEQ ID NO:21 (encoded by Genbank gene ID E59061), SCR1 of SEQ ID NO:18 (encoded by Genbank gene ID FJ939565), and SCR3 of SEQ ID NO:19 (encoded by Genbank gene ID FJ939564) to get the respective oligomers. Those oxidoreductase oligomers displayed significantly improved thermal stability and catalytic activity. The SrtA-mediated ligation can be used as a platform technique to improve enzyme stability and catalytic activity of oxidoreductases.

The first goal of the present invention is to provide oxidoreductase oligomers. The oxidoreductase oligomers are prepared through the following steps: (1) add sequence GGG and LPXTG to N-terminus and C-terminus of oxidoreductases, respectively (SCRII had a native G at its N-terminus and it is not necessary to add GGG to its N-terminus); (2) SrtA recognizes the signal sequence LPXTG at C-terminus of one oxidoreductase and cleave the amido bond between Thr and Gly to get a thioester intermediate; (3) a native Gly at N-terminus of SCRII or GGG added at N-terminus of the other oxidoreductases acts as a nucleophile to attack the thioester intermediate to make two oxidoreductases ligation through the Gly and generate an oxidoreductase oligomer.

In one embodiment, the SrtA-mediated ligation reaction should be carried out in the presence of $Ca^{2+}$.

In one embodiment, the SrtA-mediated ligation reaction is carried out at 10° C.-35° C. for 12 hr-36 hr.

In one embodiment, the SrtA-mediated ligation reaction is carried out at 25° C. for 36 hr.

In one embodiment, the oxidoreductase oligomers are carbonyl reductase oligomers.

In one embodiment, the carbonyl reductase oligomers included SCRII oligomer, CR2 oligomers, CR4 oligomers, SCR oligomers and SCR3 oligomers.

In one embodiment, the amino acid sequence of the oxidoreductase is shown in SEQ ID NO: 1 (SCRII), SEQ ID NO:18 (SCR1, encoded by gene ID FJ939565), SEQ ID NO:19 (SCR3, encoded by gene ID FJ939564), SEQ ID NO: 20 (CR2, encoded by gene ID AB183149), or SEQ ID NO:21 (CR4, encoded by gene ID E59061).

In one embodiment, SrtA recognition sequence is LPXTG (X was any amino acid), as shown in SEQ ID NO:2.

In one embodiment, signal sequence LPXTG is added to the oxidoreductase through a linker. The linker could be GGGGS (as shown in SEQ ID NO:17).

In one embodiment, sequence LPXTG is LPETG (as shown in SEQ ID NO:3).

In one embodiment, the SrtA enzyme is from *Staphylococcus aureus* genome.

In one embodiment, the amino acid sequence of SrtA is shown in SEQ ID NO:4.

The second goal of the present invention is to provide a recombinant strain expressing the oxidoreductases with SrtA recognition sequence at C terminus.

In one embodiment, the oxidoreductase includes SCRII, SCR1, SCR3, CR2 and CR4.

In one embodiment, the amino acid sequence of oxidoreductase is shown as SEQ ID NO:1.

In one embodiment, the SrtA recognition sequence is LPXTG (X could be any amino acid).

The third goal of the present invention is to provide a method for preparing (S)-PED by SCRII oligomers.

In one embodiment, 2-HAP is used as substrate to prepare (S)-PED.

In one embodiment, 100 mM potassium phosphate solution (pH 6.0), 5 g/L 2-HAP and equimolar NADPH, appropriate SCRII oligomers are mixed to prepare (S)-PED under 35° C., 200 r/min for 3 hr.

The fourth goal of the present invention is to provide a method for preparing chiral compounds using oxidoreductase oligomers.

The fifth goal of the present invention is to provide the application of oxidoreductase oligomers in fields like drugs, pesticides, hormones and food additives.

We provide a method to produce oxidoreductase oligomers. Compared to wild-type SCRII, the SCRII oligomers improved thermal stability and catalytic activity. The SrtA-mediated SCRII oligomers display a $T_m$ value 10° C. higher than that of wild-type SCRII. The SCRII oligomers are used to catalyze asymmetric transformation of 2-HAP to (S)-PED within 3 hr, with an optical purity of 100% and a yield of 99%. In addition, the SCRII oligomers have a 6-fold improvement in specific activity over that of SCRII.

SrtA is cloned from *S. aureus* genome and highly expressed in *E. coli*. SrtA recognition sequence is added to the C-terminus of SCRII using genetic techniques to obtain SCRII-mtf. SrtA and SCRII-mtf enzymes are purified and used to prepare SCRII oligomers in the presence of $Ca^{2+}$.

Wild-type SCRII catalyzes 2-HAP to (S)-PED with a low efficiency. SrtA-mediated ligation of SCRII-mtf is used to construct SCRII oligomers. The SCRII oligomers increases the specific activity by 6-fold over that of wild-type SCRII. Moreover, the thermal stability of the SCRII oligomers is significantly improved. The SCRII oligomers maintain over 90% specific activity after incubation at 50° C. for 1 hr. The biosysnthesis reaction time is reduced by 16 folds compared to that of SCRII. The oxidoreductase oligomers overcome the disadvantages of carbonyl reductase such as weak thermal stability and low transformation efficiency. The present invention provides an effective method for preparation of (S)-PED and a new direction for protein engineering of oxidoreductases.

SrtA-mediated ligation was applied to make oligomers of other oxidoreductases, such as SCRII, CR2, CR4, SCR and SCR3. Comparing to the wild type enzyme, SrtA-mediated SCR1 oligomers have improved over 8-fold of catalytic activity towards 2-HAP reduction. SCR1 oligomers had 10° C. higher $T_m$ than that of SCR1. SCR3 oligomers have displayed nearly 7-fold improved activity towards 2-HAP reduction and 10° C. higher $T_m$ compared with that of its wild-type enzyme. CR2 enzyme exhibited a specific activity of 0.93 U/mg, while CR2 oligomers showed a specific activity of 5.86 U/mg towards the reduction of acetophenone. CR2 oligomers had 5° C. higher $T_m$ than that of the wild-type CR2. CR4 oligomers have displayed 6.3-fold improved activity towards acetophenone reduction and 8° C. higher $T_m$ compared with that of its wild-type. In short, SrtA-mediated ligation can be used as a platform to improve catalytic activity and thermal stability for oxidoreductases.

EXAMPLES

Example 1. *S. aureus* Genome Extraction

LB medium (g/L): tryptone 10, yeast extract 5, NaCl 10, pH 7.0, 1.5% agar powder in solid medium. *S. aureus* strain was cultured in 5 mL liquid medium under the condition of 37° C., 200 r/min for 10 hr. After cultivation, the culture was centrifuged at 6,000 rpm for 20 min, followed by washing with 0.8% NaCl for twice and the cell pellet was collected. Genomic DNA Extraction Miniprep System (Sangon Biotech. Co., Shanghai, China) was used to extract *S. aureus* genome.

Example 2. SrtA Gene Amplification

Primers for srtA gene cloning were as follows (as shown in SEQ ID NO:5-SEQ ID NO:6):

```
SrtA_F:
                                    (SEQ ID No: 5)
CGCCATATGCAAGCTAAACCTCAAATTC

SrtA_R:
                                    (SEQ ID No: 6)
CCGCTCGAGTTTGACTTCTGTAGCTAC
```

PCR system: $ddH_2O$ 37 μL, 10× reaction buffer 5 dNTP (25 mmol/L) 0.5 μl, primers (50 pmol/μL) 1 genomic DNA 5 Taq DNA polymerase (5 U/μL) 0.5 μL.

PCR program: 98° C. 1 min; 98° C. 30 s, 55° C. 30 s, 72° C. 30 s, 30 cycles; 72° C. 10 min. With *S. aureus* genome as template, srtA gene (amino acid sequence shown as SEQ ID NO:4) was amplified. DNA fragments were purified using 3S Spin Agarose Gel DNA Purification Kit.

Example 3. Construction of a Recombinant Plasmid Containing srtA (1) Digestion of srtA and Plasmid pET21a Plasmid pET21a was Extracted Using Mini-Plasmid Rapid Isolation Kit.

$H_2O$, buffer, srtA gene or plasmid pET21a and restriction enzymes were sequentially added to an Eppendorf tube, followed by oscillation blending. After centrifugation for 2 sec, the reaction was incubated in a water bath at 37° C. for 3 hr. Restriction endonuclease reaction system was added with loading buffer (1/10) or incubated at 65° C. for 10 min to stop the enzyme digestion reaction. Restriction endonuclease product was analyzed by agarose gel electrophoresis, followed by gel extraction of the desired DNA fragments.

Reaction system (40 μL): 10× buffer H 4 μL, DNA 10 μL, Nde I 2 μL, Xho I 2 μL, $ddH_2O$ 22 μL.

(2) srtA Gene was Cloned onto Plasmid pET21a.

Reaction system (10 μL): plasmid pET21a 0.8 μL, srtA 4.2 μL, ligation solution 5 μL. The mixture was incubated at 16° C. for 12-16 hr.

(3) Recombinant Plasmid pET21a-srtA was Transformed into *E. coli* JM109.

10 μL ligation product was added to 100 μL *E. coli* JM109 competent cell suspension in each tube and the mixture was softly blended. The tube was put in ice for 30 min and then transferred to 42° C. for 90 sec heat shock. Then the system was quickly transferred to ice bath for 2 min. The mixture was added with 700 μL LB medium and cultured under the conditions of 37° C., 100 rpm for 1 hr. After cultivation, the culture was centrifuged at 3,000 rpm for 2 min and 600 μL supernatant was removed. The rest culture was distributed onto a LB solid medium containing 100 μg/mL ampicillin and incubated at 37° C. overnight.

Selection of positive clones: 4 clones were selected and transferred to 3 mL liquid LB medium containing 100 μg/mL ampicillin for cultivation at 37° C. for 12 hr. Plasmids were extracted using Mini-Plasmid Rapid Isolation Kit. The positive clone was verified by the following restriction endonuclease reaction system (20 μL): 10× Buffer H 2 μL, DNA 5 μL, Nde I 0.5 μL, Xho I 0.5 μL, and ddH₂O 12 μL. After verification, positive clone pET21a-srtA was obtained.

(4) Recombinant Plasmid pET21a-srtA was Transformed into *E. coli* BL21 (DE3)

Recombinant plasmid pET21a-srtA was added to *E. coli* BL21 (DE3) competent cell suspension and softly mixed in one tube. The mixture was incubated in ice bath for 30 min and transferred to a 42° C. water bath for 90 sec heat shock. Then the mixture was transferred to an ice bath for 2 min. The mixture was added with 700 μL LB medium and incubated under the conditions of 37° C., 100 rpm for 1 hr. After cultivation, the culture was centrifuged at 3,000 rpm for 2 min, and 600 μL supernatant was removed. The rest of the culture was spread onto a LB solid medium containing 100 μg/mL ampicillin and incubated at 37° C. overnight.

Example 4.
GGG-Oxidoreductase-GGGGSLPETGG
(Oxidoreductase-Mtf) Amplification

C. for 3 hr. Restriction endonucleases reaction system was added with Loading buffer (1/10) or incubated at 65° C. for 10 min to stop the enzyme digestion reaction. Enzyme-digested product was analyzed by agarose gel electrophoresis, followed by gel extraction of the desired DNA fragments.

Reaction system (40 μL): 10× Buffer H 4 μL, DNA 10 μL, restriction enzyme I 2 μL, restriction enzyme II 2 μL, and ddH₂O 22 μL.

(2) Oxidoreductase-Mtf Gene was Cloned onto Plasmid pET28a.

Reaction system (10 μL): plasmid pET28a 0.8 μL, oxidoreductase-mtf gene 4.2 μL, ligation solution 5 μL. The mixture was incubated at 16° C. for 12-16 hr.

(3) Recombinant Plasmid was Transformed into *E. coli* JM109.

10 μL ligation product was added to *E. coli* JM109 competent cell suspension in an Eppendorf tube and gently blended. The tube was put in ice for 30 min and transferred at a 42° C. water bath for 90 sec. After heat shock, the system was quickly transferred to an ice bath for 2 min. The

TABLE 1

Oxidoreductase-mtf primers and PCR programs

| Primers | Sequence (5'→3') | Thermal cycle detail |
|---|---|---|
| cr2-mtf_F (SEQ ID NO: 7) | CGGGATCCATGGGAGGCGGAACATTTACAGTGGTG | 98° C. for 30 s; 98° C. for 10 s, 50° C. for 15 s, 72° C. for 55 s for 30 cycles; 72° C. for 10 mm. |
| cr2-mtf_R (SEQ ID NO: 8) | CGGAATTCGCCGCCGGTTTCCGGAAGGCTGCCACCGCCACCCCCACGGTACGC | |
| cr4-mtf_F (SEQ ID NO: 9) | CGGGATCCATGGGAGGCGGAACGTTTCAGCATTTTTTAAG | 98° C. for 30 s; 98° C. for 10 s, 55° C. for 15 s, 72° C. for 45 s for 30 cycles; 72° C. for 10 mm. |
| cr4-mtf_R (SEQ ID NO: 10) | CCCTCGAGGCCGCCGGTTTCCGGAAGGCTGCCACCGCCACCAACGCAAGTGTACCCACC | |
| scr1-mtf_F (SEQ ID NO: 11) | CGGGATCCATGGGAGGCGGAAGTAAAGACGAAACAATTTC | 98° C. for 30 s; 98° C. for 10 s, 48° C. for 15 s, 72° C. for 60 s for 30 cycles; 72° C. for 10 mm. |
| scr1-mtf_R (SEQ ID NO: 12) | CCCTCGAGGCCGCCGGTTTCCGGAAGGCTGCCACCGCCACCTGGACAGTATAACCAC | |
| scrII-mtf_F (SEQ ID NO: 13) | CCCATGGGCGAAATCGAATC | 98° C. for 30 s; 98° C. for 10 s, 55° C. for 15 s, 72° C. for 45 s for 30 cycles; 72° C. for 10 mm. |
| scrII-mtf_R (SEQ ID NO: 14) | CCCTCGAGGCCGCCGGTTTCCGGAAGGCTGCCACCGCCACCTGGACAAGTGTAACCACCATC | |
| scr3-mtf_F (SEQ ID NO: 15) | CCCATATGGGAGGCGGAGGCGAAATCGAATC | 98° C. for 30 s; 98° C. for 10 s, 52° C. for 15 s, 72° C. for 45 s for 30 cycles; 72° C. for 10 mm. |
| scr3-mtf_R (SEQ ID NO: 16) | CCCTCGAGGCCGCCGGTTTCCGGAAGGCTGCCACCGCCACCTGGACAGGTGAATCCAC | |

The recognition sequence of SrtA are displayed in bold.

Example 5. Construction of Recombinant *E. coli* Containing Oxidoreductase-Mtf (1) Digestion of Oxidoreductase-Mtf Genes and pET28a Plasmid pET28a was extracted using Mini-Plasmid Rapid Isolation Kit.

H₂O, buffer, the gene or the plasmid DNA and restriction endonucleases were sequentially added to an Eppendorf tube, followed by oscillation blending. After centrifugation for 2 sec, the reaction was incubated in a water bath at 37° mixture was added with 700 μL LB medium and cultured at 37° C. with 100 rpm for 1 hr. After cultivation, the culture was centrifuged at 3,000 rpm for 2 min and 600 μL supernatant was removed. The rest of the culture was distributed onto a LB solid medium containing 50 μg/mL kanamycin, followed by incubation at 37° C. overnight.

Selection of positive clones: 4 clones for each kind of recombinant cells were selected and transferred to a 3 mL liquid LB medium containing 50 μg/mL kanamycin for cultivation at 37° C. for 12 hr. Plasmids were extracted using Mini-Plasmid Rapid Isolation Kit. The positive clones were selected by the following restriction endonuclease reaction system (20 µL): 10× Buffer H 2 µL, DNA 5 µL, restriction endonuclease I 0.5 µL, restriction endonuclease II 0.5 µL, and ddH$_2$O 12 µL. After verification by restriction enzyme digestion, the positive clone pET28a-oxidoreductase-mtf was obtained.

(4) Recombinant plasmid pET28a-oxidoreductase-mtf was transformed into *E. coli* BL21 (DE3).

Recombinant plasmid pET28a-oxidoreductase-mtf was added to *E. coli* BL21 (DE3) competent cell suspension and softly mixed. The mixture was incubated in an ice bath for 30 min and transferred to a 42° C. water bath for 90 sec. After heat shock, the mixture was transferred to an ice bath for 2 min. The mixture was added with 700 µL LB medium and cultured at 37° C. with 100 rpm for 1 hr. After cultivation, the culture was centrifuged at 3,000 rpm for 2 min, and 600 µL supernatant was removed. The rest of the culture was spread onto a LB solid medium containing 50 µg/mL kanamycin and was incubated at 37° C. overnight.

Example 6. The Expression of Recombinant *E. coli*/pET28a-Oxidoreductase-Mtf LB medium (g/L): tryptone 10, yeast extract 5, NaCl 10, pH 7.0, when necessary, 100 µg/mL ampicillin or 50 µg/mL kanamycin was added. LB solid medium was prepared with addition of 1.5% agar powder into the LB medium. Positive *E. coli*/pET28a-oxidoreductase-mtf clones were cultured in 10 mL LB liquid medium containing 100 µg/mL ampicillin or 50 µg/mL kanamycin at 37° C. with 200 rpm overnight. Then the culture was transferred to 1 L LB medium containing 100 µg/mL ampicillin or 50 µg/mL kanamycin at 37° C. with 200 rpm until OD$_{600}$=0.6. IPTG was added into the culture with final concentration of 0.1 mM. Then the culture was incubated at 30° C. for 10 hr.

Example 7. Purification of SrtA and Oxidoreductase-Mtf

The recombinant *E. coli*/pET28a-oxidoreductase-mtf was centrifuged for the cell collection. The collected cells were washed with 0.8% NaCl solution for three times. The cells were resuspended with 20 mM Tris-HCl (pH 8.0) and subjected to ultrasonication for cell disruption. The disrupted cells were centrifuged at 10,000×g for 2 mM, at 4° C. to collect supernatant. The crude enzyme was obtained after the supernatant was filtrated with a 0.22 µm membrane. The crude enzyme was first loaded on a Ni-NTA column with binding buffer (20 mM Tris-HCl, 150 mM NaCl, 1 M imidazole, pH 8.0). After the crude enzyme was washed with 200 ml 30 mM imidazole, the target protein was eluted with 200 mM imidazole in the binding buffer. Then the elution was loaded to a Superdex 200 column with a binding buffer (20 mM Tris-HCl, 150 mM NaCl, pH 8.0). The elution from the Superdex 200 column was collected and analyzed by SDS-PAGE.

Example 8. SrtA-Mediated Oligomerization (1) Optimization of Ligation Reaction Using SrtA-Mediated Oligomerisation of SCRII SrtA (25 µmol/L) and SCRII-mtf (30 µmol/L) were added to ligation buffer (50 mM Tris-HCl, 150 mM NaCl, 10 mM CaCl$_2$, pH 7.5). The ligation reaction was carried out at 10° C., 15° C., 20° C., 25° C., 30° C., 35° C. for 8 hr. The mixture containing SrtA and SCRII was used as a control. SDS-PAGE analysis revealed that the optimal ligation temperature was 25° C. The reaction was carried out at 25° C. for 12 hr, 24 hr and 36 hr, respectively. According to the yield of SrtA-mediated ligation products, the optimal ligation time was 36 hr. The optimal condition, temperature 25° C. and the ligation duration 36 hr, was then used to construct other oxidoreductase oligomers.

(2) Separation of Oligomers

Once ligation reaction was completed, the mixture was concentrated to 500 µL. The concentrated mixture was applied to a Superdex 200 column which was equilibrated with a binding buffer (50 mM Tris-HCl, 150 mM NaCl, pH8.0). Oxidoreductase oligomers were eluted from the column and analyzed by SDS-PAGE.

Example 9. Determination of the Enzyme Activity

The enzyme assay system (100 µL) contained 100 mM potassium phosphate buffer (pH 6.0), 0.5 mM NADPH and 5 mM substrate. The solution was incubated at 35° C. for 3 min After the addition of appropriate enzymes, the absorbance change was scanned using a 340 nm microplate reader. Every assay was repeated for three times and the average value was calculated. One enzyme activity unit (U) was defined as enzyme volume for catalyzing the oxidation of 1 µmol NADPH per minute. Protein concentration was determined using Bradford method with BSA as standard protein. Specific activity was defined as enzyme activity (U)/protein volume (mg).

Specific activities of SCRII (SCR1, SCR3, CR2 and CR4) and their oligomers towards 2-HAP or acetophenone were determined under the same condition. Specific activity of SCRII was 6.3 U/mg. SCRII oligomers had the highest specific activity of 38.5 U/mg, 6-fold improvement compared to that of SCRII. SCR1 and its oligomers showed specific activities of 1.05 U/mg and 8.31 U/mg towards 2-HAP, respectively. SCR3 and its oligomers displayed specific activities of 2.11 U/mg and 14.20 U/mg towards 2-HAP, respectively. CR2 and its oligomers showed specific activities of 0.93 U/mg and 5.86 U/mg towards acetophenone, respectively. CR4 and its oligomers showed specific activities of 5.81 U/mg and 36.81 U/mg towards acetophenone, respectively.

Example 10. pH Tolerance and Thermal Stability of SCRII Oligomers

The optimal temperature and pH of SCRII, SCRII-mtf and SCRII oligomers were determined. The three enzymes were incubated at different temperatures (10-60° C.) for 1 hr. And their specific activity was determined to evaluate their thermostability. These three enzymes were subjected to solutions with different pHs (4.0-9.0) for 24 hr, and their specific activity was determined to determine their pH tolerance.

SCRII and SCRII-mtf had similar temperature and pH dependence. With increase of temperature. The specific activities of SCRII and SCRII-mtf were increased until 35° C. The specific activity decreased quickly when temperature was higher than 35° C. SCRII oligomers displayed similar activity between 20° C. and 60° C. With increase of temperature, the specific activity of SCRII oligomer was increased until 50° C. When the temperature was higher than 50° C., its specific activity began to decrease. SCRII, SCRII-mtf and SCRII oligomers had similar pH dependence. SCRII and SCRII-mtf gave the best performance at pH 6.0 while SCRII oligomers performed the best at pH 6.0 and pH 6.5.

SCRII and SCRII-mtf remained about 80% of the specific activity after they were incubated at 40° C. for 1 hr, but less than 20% at 50° C. SCRII oligomers remained 90% of the specific activity after it was incubated at 40° C. for 1 hr. These three enzymes had similar pH tolerance. They all remained over 75% of specific activity when they are incubated in the buffer with pH 5.0-9.0 for 24 hr.

Example 11. Determination of Kinetics Parameter

Kinetics parameters of SCRII, SCRII-mtf and SCRII oligomers towards 2-HAP were determined. The assay solution consisted of 100 mM potassium phosphate buffer (pH 6.0), 5 mM NADPH, 0.5-20 mM 2-HAP and appropriate enzymes, with a total volume of 100 µL. Every assay was repeated for three times to determine an average value. Kinetics parameters were derived from Michaelis-Menten and Lineweaver-Burk equation. SCRII, SCRII-mtf and SCRII oligomers displayed $K_m$ values of 4.52, 3.98 and 1.40, respectively. SCRII oligomers showed 3.3-fold decrease compared to SCRII. SCRII and SCRII-mtf had similar $V_{max}$ value of 32.17 U/mg and 33.00 U/mg, resulting in similar $k_m$ values. SCRII oligomers displayed the highest $V_{max}$ of 42.72 U/mg. These results showed that SCRII oligomers had the lowest $K_m$ and highest $k_m$ values.

Example 12. Asymmetric Reduction

SCRII, SCR1, SCR3, CR2 and CR4 and their oligomers were used to asymmetrically reduce their respective substrates. Reaction system consisted of potassium phosphate buffer (pH 6.0), 5 g/L substrate, equimolar NADPH and appropriate enzyme (about 1 mg/mL), with a total volume of 2 mL. The reaction was carried out under the condition of 35° C., with 200 r/min shaking for 6 hr. Every experiment was repeated for three times.

Once the reaction was completed, supernatant was added with 2× volume of ethyl acetate to extract the products. The organic phase was used for HPLC analysis on a Chiralcel OB-H column (Daicel Chemical Ind. Ltd., Japan) with hexane/isopropanol (v/v, 9:1) as the mobile phase. Flow rate was 0.5 mL/min Detection wavelength was 215 nm. The optical purity and yield of products were measured using the following equations:

$(S)$-PED optical purity=$[(C_S-C_R)/(C_S+C_R)] \times 100\%$ $(R)$-1-phenethyl alcohol optical purity=$[(C_R-C_S)/(C_S+C_R)]$ $(S)$-PED yield (%)=$C_S/C_0 \times 100\%$ $(R)$-1-phenethyl alcohol yield (%)=$C_R/C_0 \times 100\%$ $C_S$ means concentration of (S)-configuration, $C_R$: concentration of (R)-configuration, $C_0$: initial concentration of substrate.

SCRII and its oligomers catalyzed the conversion of 2-HAP to (S)-PED with yields of 43% and >99% in 3 hr, respectively. SCRII oligomers reduced reaction time by 16 folds compared to SCRII. SCR1 and its oligomers catalyzed the conversion of 2-HAP to (S)-PED with yields of 30% and 97% in 6 hr. SCR3 and its oligomers converts 2-HAP to (S)-PED with yields of 99% and 46% in 6 hr, respectively. CR2 and its oligomers catalyzed the conversion of acetophenone to (R)-1-phenyl ethanol with yields of 25% and 65%, respectively. CR4 and its oligomers converted acetophenone to (R)-1-phenyl ethanol with yields of 79% and >99%, respectively. The oxidoreductases and their oligomers showed the similar optical purity of 99%-100%. The results suggested that SrtA-mediated oligomers improved the biotransformation efficiency without affecting their stereoselectivity.

The present invention has been described in some details for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A carbonyl reductase oligomer, wherein said carbonyl reductase oligomer comprises two of the same carbonyl reductase polypeptide, wherein the C-terminus of a first carbonyl reductase polypeptide is connected to the N-terminus of a second carbonyl reductase polypeptide by a sortase A (Srt A) recognition sequence via a Srt A mediated ligation mechanism, wherein said carbonyl reductase is selected from a group consisting of SCRII of SEQ ID NO: 1, SCR1 of SEQ ID NO:18, SCR3 of SEQ ID NO:19, CR2 of SEQ ID NO:20, and CR4 of SEQ ID NO:21; and wherein said carbonyl reductase oligomer has higher specific activity than that of the wild-type counterpart enzyme.

2. The carbonyl reductase of claim 1, wherein said Srt A recognition sequence is LPXTG, wherein X is any amino acid moiety.

3. The carbonyl reductase oligomer of claim 1, wherein said oxidoreductase oligomer is prepared as follows:

(1) obtaining the first carbonyl reductase polypeptide with said SrtA recognition sequence added to its C-terminus;
(2) using SrtA to cleave said SrtA recognition sequence to obtain a thioester intermediate; and
(3) using said thioester intermediate of the first carbonyl reductase polypeptide to react with a Gly at the N-terminus of the second carbonyl reductase to form said carbonyl reductase oligomer.

4. The carbonyl reductase oligomers of claim 3, wherein step (3) is carried out in the presence of $Ca^{2+}$.

5. The carbonyl reductase oligomer of claim 1, wherein said SrtA is from *Staphylococcus aureus*.

6. A method for preparing chiral alcohols, comprising contacting a carbonyl reductase substrate with the carbonyl reductase oligomer of claim 2 to produce said chiral alcohol.

7. The method of claim 6, wherein the chiral alcohols are (S)-1-phenyl-1,2-ethanediol or (R)-1-phenethyl alcohol.

* * * * *